United States Patent [19]

Maurer et al.

[11] 3,930,494

[45] Jan. 6, 1976

[54] METHOD AND APPARATUS FOR THE INDIRECT MEASUREMENT OF BLOOD PRESSURE

[75] Inventors: Alan H. Maurer, Philadelphia; John J. Swana, Audubon; Richard F. Vanderpool, Spring City, all of Pa.

[73] Assignee: General Electric Company, New York, N.Y.

[22] Filed: Sept. 20, 1971

[21] Appl. No.: 181,772

[52] U.S. Cl............................................ 128/2.05 A
[51] Int. Cl.²................................................ A61B 5/02
[58] Field of Search.... 128/2.05 A, 2.05 M, 2.05 Q, 128/2.05 R, 2.05 S, 2.05 Z

[56] References Cited
UNITED STATES PATENTS

| | | | |
|---|---|---|---|
| 3,085,567 | 4/1963 | Vigilante | 128/2.05 A |
| 3,318,303 | 5/1967 | Hammacher | 128/2.05 S |
| 3,450,131 | 6/1969 | Vogt | 128/2.05 A |

FOREIGN PATENTS OR APPLICATIONS

| | | | |
|---|---|---|---|
| 102,840 | 10/1941 | Sweden | 128/2.05 S |

*Primary Examiner*—William E. Kamm

[57] ABSTRACT

A method and apparatus for automatically detecting the blood pressure of a person by auscultation in which a standard blood pressure cuff is connected to a pressure transducer for providing a pressure signal and a microphone is used for providing an electrical signal from the Korotkoff sounds detected. The Korotkoff sound electrical signal is amplified and passed through a bandpass filter which has a flat response between approximately 50 and 160 Hz and a sharp cutoff below 50 Hz. The resultant signal is then summed with the pressure signal to provide an output which indicates the pressures at which the five phases associated with the Korotkoff sounds occur.

9 Claims, 4 Drawing Figures

3,930,494

METHOD AND APPARATUS FOR THE INDIRECT MEASUREMENT OF BLOOD PRESSURE

BACKGROUND OF THE INVENTION

In many instances it is highly desirable from an economic and convenience standpoint to be able to accurately measure the blood pressure of an individual without the use of a doctor or nurse. To this end, automatic blood pressure measuring devices have been developed, some of which involve detection of Korotkoff sounds. However, the degree of correlation between blood pressure readings taken automatically by these prior art devices and similar readings taken by a doctor is not as high as is desirable. It is well known that a blood pressure reading for an individual may vary depending on the method used to measure the blood pressure. For example, measurement of blood pressure by the use of a catheter inserted in a blood vessel may result in a significantly different reading than blood pressure measured by the standard auscultation technique. Since most diagnosis using blood pressure measurement is based on a doctor's knowledge and experience and reference material regarding blood pressure measurements taken by the standard auscultation technique, it is highly desirable to have readings from an automatic blood pressure measuring device come as close as possible to readings made by a doctor using the standard auscultation technique. Also, it is desirable to have blood pressure measurements include all information which might be needed by a doctor including indication of Phase IV as well as Phase V Korotkoff sounds. Particularly, controversy centers over whether the Phase IV of the Korotkoff sounds (the period marked by the distinct, abrupt muffling of sound) or Phase V (the point at which sounds disappear) should be utilized to determine the diastolic pressure. The American Heart Association in its 1967 report recommends that whenever possible both the Phase IV and Phase V pressures should be recorded. Therefore, it is highly desirable to have blood pressure measuring apparatus which indicates both the Phase IV and Phase V pressures, where possible.

SUMMARY OF THE INVENTION

Thus, it is an object of the subject invention to provide a process and apparatus for measuring the blood pressure of an individual which closely correlates with measurements made using the standard auscultation technique.

Another object of the subject invention is to provide a process and apparatus for automatically measuring blood pressure which will provide readily discernible indications of both phase IV and phase V pressures, where possible.

The above-mentioned objects are realized in the subject invention by providing a process, and apparatus for performing the process, comprised of the steps of inflating a blood pressure cuff to a pressure above the point at which the radial pulse disappears; releasing the pressure at a substantially linear rate of 2–3 mm Hg/sec; sensing the pressure exerted by the cuff and converting this to a first electrical signal; sensing the Korotkoff sounds and converting this to an amplified, second electrical signal; filtering the second signal to allow a bandpass having a sharp low frequency cutoff of no less than 45 Hz; and, in the preferred embodiment, summing the filtered, second signal with the first signal to produce a composite signal indicating the pressures at which the phases associated with the Korotkoff sounds occur. It is critical that the cutoff of frequencies below the low frequency cutoff be sharp to promote accurate indication of the phases associated with Korotkoff sounds.

The subject matter which is regarded as the present invention is particularly pointed out and distinctly claimed including portions of this specification.

BRIEF DESCRIPTION OF THE DRAWINGS

The present invention, however, both as to organization and method of operation, together with further objects and advantages thereof, may best be understood by reference to the following description taken in connection with the accompanying drawing in which.

DESCRIPTION OF THE PREFERRED EMBODIMENTS

The most commonly accepted blood pressure measurement method is the auscultation technique recommended by the American Heart Association. In this technique a stethoscope is placed on the skin adjacent a blood pressure cuff and the pressure is raised in the cuff approximately 30 mm Hg above the point at which the radial pulse disappears and then released at a rate of from 2–3 mm Hg/sec. As the pressure falls, the Korotkoff sounds becomes audible and pass through four audible phases as the pressure declines. Phase I is the period marked by the first appearance of faint, clear tapping sounds which gradually increase in intensity. Phase II is the period during which a murmur of swishing quality is heard. Phase III is the period during which sounds are crisper and increase in intensity. Phase IV is the period marked by the distinct, abrupt muffling of sound so that a soft, blowing quality is heard. Phase V is the point at which the sounds disappear. It is generally accepted that the systolic pressure is read as the pressure at which the first sound (Phase I) is heard. There is presently some controversy as to whether the muffling sound (Phase IV) or the disappearence of sound (Phase V) should be used as the index of diastolic pressure. Generally, however, it recommended that both Phase IV and Phase V pressures be recorded.

Figure 1:
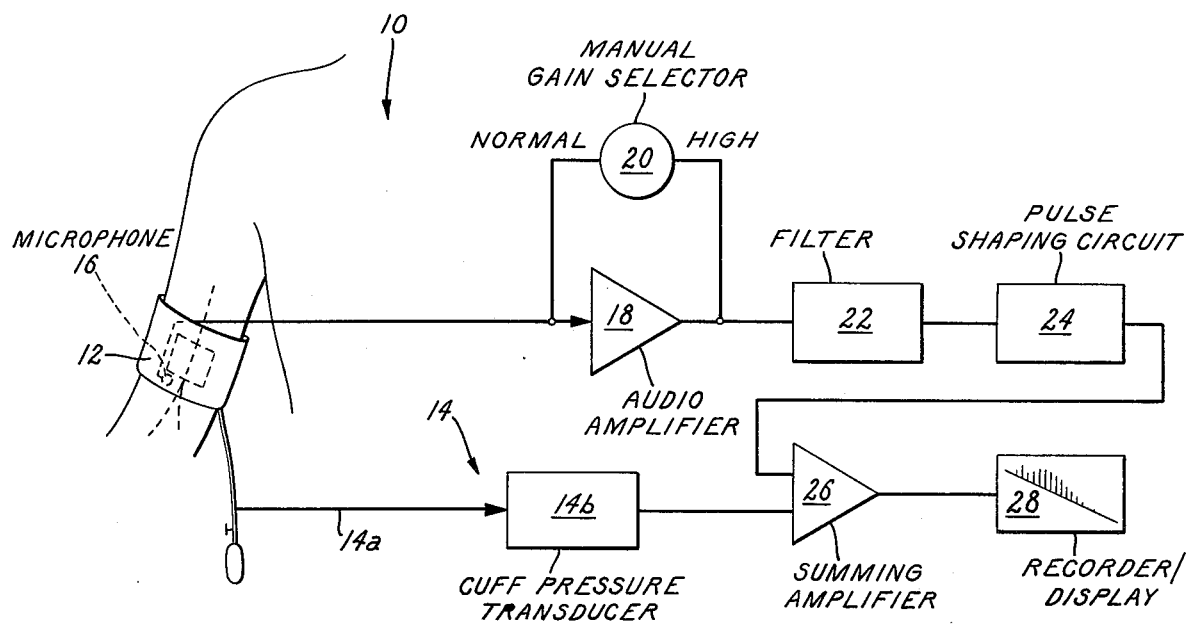
FIG. 1 is a block diagram of the apparatus of the subject invention.

The subject invention, as shown in FIG. 1, is a process and apparatus for automatically measuring the blood pressure of an individual which has been demonstrated to give readings of high correlation with measurements taken by a trained operator using the standard auscultation technique. In general, the apparatus 10 of the subject invention in its preferred embodiment includes a standard blood pressure cuff 12; means 14 for sensing the pressure in the cuff and converting this to the first electrical signal; means 16, such as a microphone, for sensing the Korotkoff sounds and converting this to a second electrical signal; an amplifier 18 for amplifying the second electrical signal (possibly including a gain control 20); a bandpass filter 22 for filtering out all but a desired range of frequencies in the amplified second signal; a pulse shaping circuit 24 for enhancing certain characteristics of the filtered, second signal, a summing amplifier for combining the first and second electrical signals so as to superimpose the signal indicating the Korotkoff sounds on the signal indicating the pressure; and means 28 for indicating and preferably recording the combined signal.

The blood pressure cuff 12 can be any standard, inflatable blood pressure cuff which is normally used in the measurement of blood pressure by auscultation. Any suitable means may be used to inflate and deflate the cuff such as a standard squeeze bulb with valve. If desired, the cuff can be inflated automatically by means of a pressurized air supply and deflated by a linear bleed valve which permits the pressure to decrease substantially linearly at a rate of 2–3 mm Hg/sec.

Pressure measuring means 14 may conveniently be comprised of a tube 14a connecting the inflatable portion of cuff 12 to a standard pressure transducer 14b which converts the pressure signal into the first electrical signal. Alternatively, any other type of state-of-the-art pressure transducer, such as a piezo-electric crystal placed within cuff 12, may be utilized.

Korotkoff sound sensing means 16 is preferably a commercially available, audio, contact microphone having a reasonably flat frequency response at least in the frequency range of 45–200 Hz. The microphone is preferably placed between the cuff and the biceps of the individual, assuming, of course, that the blood pressure is being taken on the arm of the individual. The output of the microphone, i.e. the second electrical signal, is connected to audio amplifier 18 which may be any state-of-the-art audio amplifier having a reasonably flat frequency response in the frequency range of 45–200 Hz. Preferably, gain selector 20 for amplifier 18 is provided to permit greater amplification where the Korotkoff sounds are weak. The gain selector may be continuously variable or have two or more preselected gains.

Figure 2:
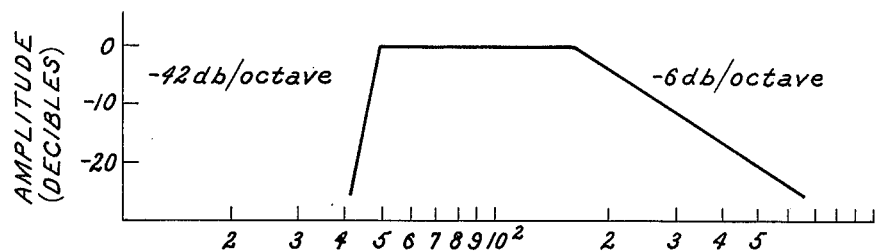
FIG. 2 is a graph showing the frequency characteristics of the preferred embodiment of bandpass filter utilized in the subject invention.

Of critical importance is the bandpass characteristics of filter 22. In the preferred embodiment, the output of filter 22 is substantially flat from 50–160 Hz with a slope of no less than 42 db/octave below 50 Hz and 6 db/octave above 160 Hz, as shown in FIG. 2. Of primary importance is the sharp cutoff of frequencies below the low frequency cutoff which aids in the proper detection of the Phase I, Phase IV and Phase V sounds. The great majority of Korotkoff sound energy lies below 45–55 Hz. It has been found experimentally that significant subaudible Korotkoff sounds consisting almost exclusively of frequency components less than 45–55 Hz occur before Phase I Korotkoff sounds can be detected by trained personnel using a stethoscope in the standard auscultation technique. These low frequencies are not detected using the standard technique probably because of the limited frequency response of stethoscopes and because the ear is relatively insensitive to flow frequency sounds. Since the peak for phase I sounds extends only to about 60 Hz and falls off rapidly, it is necessary for the filter to pass, substantially unattenuated, some frequencies below 60 Hz. Phase III Korotkoff sounds have substantial components below 45–55 Hz and between 60 and 180 Hz. The muffling, which is characteristic of phase IV sounds, results from a relatively small percentage change of energy in the frequencies from 60 to 180 Hz. Therefore, the elimination of almost all the low frequency energy below 45–55 Hz by the steep slope of the filter below 45–55 Hz allows the sudden decrease of energy in the range of 60 to 180 Hz to account for a greater percentage of the total energy decrease than if the low frequency sounds were not attenuated, thereby helping to emphasize Phase IV indication. Post-diastolic pulses which tend to consist of pulses having frequency components less than 45–55 Hz are also eliminated by providing a sharp cutoff below 45–55 Hz.

Thus, it has been found that in order to provide results which provide very high correlation with blood pressure measurements taken by the standard auscultation technique and to provide enhancement of the detection of Phases I, IV and V, and bandpass filter having a substantially flat output from 50–160 Hz with a sharp cutoff below 50 Hz and a gradual cutoff above 160 Hz is needed. While 50 Hz has been found to be the most preferable low frequency cutoff, a low frequency cutoff of between 45 and 55 Hz may alternatively be utilized. Of course, a steep slope cutoff would also be necessary. The lower the low frequency cutoff deviates from the 50 Hz, the greater the possibility of error in detecting Phase I, IV and V sounds. The higher the low frequency cutoff is above 50 Hz, the greater is the possibility of loss of detection of phase I sounds. The upper limit of the bandpass filter is not as critical as the low frequency cutoff. The bandwidth passed by the filter should include substantial frequency components of the Phase I and Phase III sounds. Particularly, the high frequency components of the Phase III sounds, i.e. those greater than 60 Hz, must be passed as it is the decrease in amplitude of these frequency components which accounts for the muffled sound indicative of Phase IV. As the particular frequency components of Phase III sounds vary from individual to individual and from time to time, a minimum high frequency cutoff is about 100 although approximately 160 Hz is preferable. The gradual roll-off of about 6 db/octave is provided to make sure that the muffling of the Phase III sounds can be detected and to eliminate any inteference due to spurious signals having frequency components much in excess of 160 Hz.

Pulse shaping circuit 24 is primarily used to aid in discrimination of Phase IV sounds by allowing small signals to pass when the Phase I, II and III sounds are detected, but not allowing a small signal to pass after the Phase III sounds have been detected. This circuitry is explained in greater detail in the discussion below regarding FIG. 4.

Amplifier 26 is a conventional state-of-the-art summing amplifier which permits superposition of the second electrical signal (indicative of the Korotkoff sounds) onto the first electrical signal (indicative of the pressure in the cuff).

The resultant combined signal may be displayed on a suitable recorder, such as a conventional strip chart recorder or might be recorded or displayed using any suitable conventional state-of-the-art apparatus. Although not preferred, alternatively the two signals may be recorded or displayed separately, such as on a two channel strip recorder.

Figure 3:
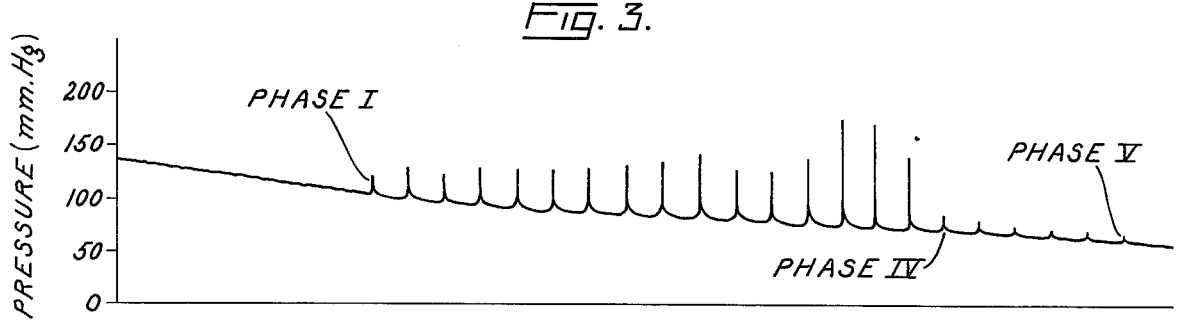
FIG. 3 is a reproduction of a strip chart recording of a blood pressure analysis of individual utilizing the process and apparatus of the subject invention.

The operation of the preferred process and apparatus of the subject invention begins with inflating blood pressure cuff 12 which is located on an extremity of the individual to be tested, to a pressure approximately 30 mm Hg above the point at which the radial pulse disappears, i.e. significantly above the approximate expected systolic pressure. The pressure is then released at a substantially linear rate of from 2–3 mm Hg/sec with the pressure in the cuff being measured by means 14 and Korotkoff sounds being detected by means 16. The second electrical signal, i.e. the Korotkoff sound signal coming from the microphone, goes to amplifier 18 and passes through bandpass filter 22. This filtered signal is then passed through pulse shaping circuit 24 and is summed with the first signal from pressure measuring means 14 to provide a combined signal which can be recorded or displayed. FIG. 3 shows an actual record of a test of the preferred embodiment apparatus in accordance with subject invention. The characteristics of Phases I, IV and V, as indicated in FIG. 3, can readily be detected. For this case the blood pressure is read as 104/66/60.

Figure 4:
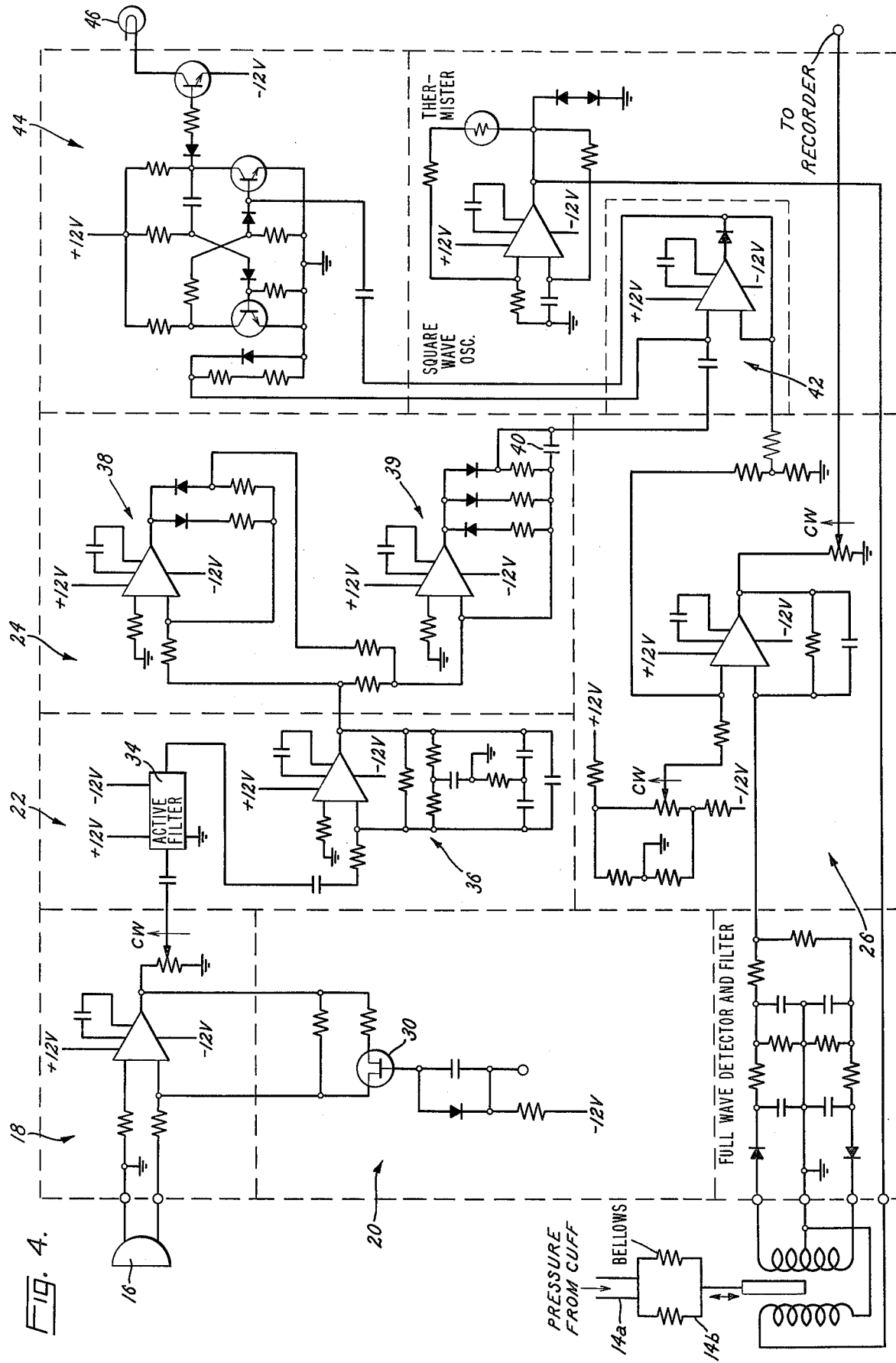
FIG. 4 is a circuit diagram of one embodiment of electrical circuits forming part of the subject invention.

FIG. 4 is a diagram of the preferred embodiment of electrical circuits that may be used in the apparatus in the subject invention. The general operation of the circuits is discussed below.

The second electrical signal coming from microphone 16 is amplified by amplifier 18. Gain selector 20 including transistor 30 provides a gain increase, preferably about 3:1 to provide high sensitivity for subjects with quiet Korotkoff sounds. The amplified Korotkoff sounds are then passed through bandpass filter 22 whose output characteristics are discussed above. The low frequency cutoff and slope is provided by active filter 34, and the high frequency cutoff and slope is set by a bandpass filter amplifier 36. The output of bandpass filter 22 is fed to pulse shaping circuit 24 which includes a full wave detector comprised of amplifiers 38 and 39 and capacitor 40 which aid in the discrimination of Phase IV sounds as described above in regard to the pulse shaping circuit 24. The change is voltage on capacitor 40 and hence the output of amplifier 42, is the difference between the voltage present on capacitor 40 and the output of amplifier 39. Before the first sound occurs (Phase I), the voltage on capacitor 40 is near zero, at the system noise level, so that occurrence of a small signal can be detected. Before a muffled sound occurs (Phase IV), capacitor 40 is charged to a relatively high voltage so that a small signal would not be detected. The muffled pulse is small because of the action of bandpass filter 22. Amplifier 42 is a differentiator that produces only positive output pulses for the summing amplifier 26 and the monostable multivibrator 44 which drives an indicator light 46 to provide the operator with a visual indication of the presence of Korotkoff sounds.

It should be noted that the apparatus and process of the subject invention provide blood pressure measurements which very closely correlate with those obtained by trained operators utilizing the standard auscultation technique. This is of great importance as the standard auscultation technique is the one most widely used. Diagnosis using blood pressure measurements is based on clinical and personal experience of doctors over many years using the standard auscultation technique. This is true even though measurements made by the standard auscultation technique may vary considerably from those obtained by other methods such as the direct method using a catheter inserted into the blood vessel. Additionally, the apparatus and process of the subject invention provide for enhancement of detection of the Phase I, IV and V sounds which improves the accuracy with which the blood pressure measurement can be read.

It is obvious that many modifications may be made within the true scope and spirit of the subject invention.

It is intended that the subject invention be limited only by the appended claims.

We claim:

1. In a process for automatically measuring the blood pressure of a person comprised of inflating a blood pressure cuff to a pressure above the point in which the radial pulse disappears; releasing the pressure at a substantially linear rate of from 2–3 mm Hg/sec.; sensing the pressure exerted by the cuff and converting this to a first electrical signal; and sensing the Korotkoff sounds and converting this to an amplified second electrical signal, wherein the improvement comprises:
    filtering the second signal to provide a passband with a low frequency cutoff of no less than 45 Hz with a sharp cutoff slope and a high frequency cutoff of no less than 100 Hz with a gradual slope; and indicating said first and second signals.

2. A process as in claim 1 wherein the low frequency cutoff is of no less than 50 Hz with a sharp slope.

3. A process as in claim 2 wherein the slope of the low frequency cutoff is no less than 42 db/octave.

4. A process as in claim 3 wherein the high frequency cutoff of the filtering step is 160 Hz with a slope of at least 6 db/octave.

5. A process as in claim 1 wherein the high frequency cutoff is no less than 160 Hz with a gradual cutoff slope.

6. A process as in claim 1 including the step of summing said first and second signals to form a composite signal before providing indication thereof.

7. An apparatus for automatically measuring the blood pressure of a person comprised of an inflatable blood pressure cuff, means for measuring the pressure in the cuff and converting it to a first electrical signal, and means for sensing the Korotkoff sounds and converting it to a second electrical signal, the improvement comprising:
    means for filtering said second signal, said means have a low frequency cutoff of no less than 45 Hz with a sharp cutoff slope and have a high frequency cutoff of no less than 100 Hz with a gradual cutoff slope; and
    means for providing indication of said first signal and said filtered second signal.

8. An apparatus for automatically measuring the blood pressure of a person comprised of an inflatable blood pressure cuff, means for measuring the pressure in the cuff and converting it to a first electrical signal, and means for sensing the Korotkoff sounds and converting it to a second electrical signal, the improvement comprising:
    means for filtering said second signal, said means have a low frequency cutoff of 50 Hz with a cutoff slope of no less than 42 db/octave and have means for providing indication of said first signal and said filtered second signal.

9. An apparatus for automatically measuring the blood pressure of a person comprised of an inflatable blood pressure cuff, means for measuring one pressure in the cuff and converting it to a first electrical signal, and means for sensing the Korotkoff sounds and converting it to a second electrical signal, the improvement comprising:
    means for filtering said second signal, said means have a low frequency cutoff of no less than 45 Hz with a sharp cutoff slope means for providing indication of said first signal and said filtered second signal and
pulse shaping means connected to the output of said filtering means for emphasizing the change in signal strength due to the muffling of said second signal associated with Phase IV of the Korotkoff sounds.

* * * * *